United States Patent [19]

Tanaka et al.

[11] Patent Number: 5,075,138

[45] Date of Patent: Dec. 24, 1991

[54] COLD AND HOT AIR SUPPLY FOR COATING POWDERY OR GRANULAR MATERIAL

[75] Inventors: Nagahiko Tanaka, Sakado; Narimichi Takei, Sugito; Kazuomi Unosawa, Adachi, all of Japan

[73] Assignee: Freund Industrial Co., Ltd., Japan

[21] Appl. No.: 599,697

[22] Filed: Oct. 18, 1990

[30] Foreign Application Priority Data

Oct. 20, 1989 [JP] Japan .................................. 1-273337

[51] Int. Cl.⁵ .............................................. B05D 7/00
[52] U.S. Cl. .................................... 427/213; 118/303; 118/DIG. 5; 241/39; 241/5
[58] Field of Search ......... 427/213; 118/303, DIG. 5; 241/39, 5, 57

[56] References Cited

U.S. PATENT DOCUMENTS

| | | | |
|---|---|---|---|
| 2,561,394 | 7/1951 | Marshall | 427/213 |
| 3,903,839 | 9/1975 | Rowe et al. | 118/303 X |
| 4,532,155 | 7/1985 | Golant et al. | 118/DIG. 5 |
| 4,556,175 | 12/1985 | Motoyama et al. | 241/57 |
| 4,656,056 | 4/1987 | Levenberger | 118/303 X |

FOREIGN PATENT DOCUMENTS 0179943  5/1989  European Pat. Off. .

Primary Examiner—Shrive Beck
Assistant Examiner—Alain Bashore
Attorney, Agent, or Firm—Kane, Dalsimer, Sullivan, Kurucz, Levy, Eisele and Richard

[57] ABSTRACT

A granulating and coating method using the drying air streams to effectuate granulating, coating and drying and apparatus therefore wherein:

a nozzle for supplying an article to be coated and another nozzle for supplying a coating material are provided at such positions that the article to be coated and the coating material collide with each other before the article to be coated and the coating material are dispersed by the drying air streams.

cold air is supplied into a region where the article to be coated and the coating material collide with each other and hot air is supplied to a region spaced in the downstream direction farther apart from the nozzles for supplying the article to be coated and the coating material than the region of the cold air supply, and the cold air supplying opening is provided around the nozzles for supplying the article to be coated and the coating material and a hot air supplying opening is provided at a region spaced farther apart from the nozzles for supplying the article to be coated and the coating material than the cold air supplying opening.

10 Claims, 3 Drawing Sheets

COLD AND HOT AIR SUPPLY FOR COATING POWDERY OR GRANULAR MATERIAL

BACKGROUND OF THE INVENTION

1. Field of the Invention

This invention relates to a granulating and coating technique, and more particularly to a technique effective in use for granulating, coating, drying and the like of a powdery or granular material having a relatively minute particle diameter.

2. Related Art Statement

As the granulating and coating technique of the type described, there has been such a technique that spray nozzles for supplying a raw powdery or granular material as being an article to be coated and a coating liquid as being a coating material are opposed to each other in an apparatus such as described in European Patent No. 0179943.

However, in the above-described technique, the article to be coated and the coating material collide with each other in directions opposed to each other. And, in a system of colliding in the opposed directions, due to an imbalance between the sprayings, either one of the two collision force tends to be stronger than that of the other.

For example, when the blow-out force of the coating liquid is stronger, the coating material adheres to the inner wall surface opposed thereto and is solidified thereat in the apparatus. In that case, before the coating material solidifys, the article to be coated may adhere onto the coating material and be accumulated thereat.

Furthermore, there may occur such a disadvantage that, due to the imbalance between the blow-out forces and/or the blow-out flow rates, the coating liquid is solidified into particles without adhering to and being coated on the article to be coated; so-called "spray dry phenomenon".

Further, the inventors of the present invention have found that, in the normal granulating and coating technique such as U.S. Pat. No. 4,556,175 in which only the hot air is supplied as the drying air stream, the above-described "spray dry phenomenon" may occur even when the spray nozzles are not opposed to each other.

SUMMARY OF THE INVENTION

It is an object of the present invention to provide a technique capable of performing efficient and reliable granulating and coating.

It is another object of the present invention to provide a technique in which a coating material does not adhere to an opposed inner wall surface or is not solidified thereat, or the coating material is prevented from solidifying into particles due to "spray dry phenomenon".

The above-described and other objects and novel characteristics of the present invention will become apparent from description of this specification and the accompanying drawings.

Outlines of typified aspects of the invention disclosed in the present application will hereunder be briefly described.

More specifically, in the granulating and coating method according to the present invention, cold air is supplied to the region where the article to be coated and the coating material collide with each other, and hot air is supplied to the region spaced farther apart from the means for supplying the article to be coated and the coating material than the region of the cold air supply.

Furthermore, the granulating and coating apparatus according to the present invention is constructed such that a cold air supplying means is provided outside the means for supplying the article to be coated and the coating material, and a hot air supplying means is provided at a position spaced in the downstream side farther apart from the both means for supplying the article to be coated and the coating material than the cold air supplying means.

The above-described cold air supplying means may be formed of a porous cold air supplying opening annularly provided outside the both means for supplying the article to be coated and the coating material.

Further, the above-described hot air supplying means may be formed of a porous hot air supplying opening annularly provided outside the cold air supplying opening.

According to the granulating and coating method and the apparatus therefor of the present invention, only the cold air is supplied to the region where the article to be coated and the coating material collide with each other, but no hot air is supplied thereto. Therefore, such a disadvantage is obviated that, before colliding with the article to be coated, the coating material is evaporated by the hot air, and only the coating material is solidified into particles due to the "spray dry phenomenon". Thus, the efficient granulating and coating can be effected.

DETAILED DESCRIPTION OF THE INVENTION

Embodiment 1

Figure 1:
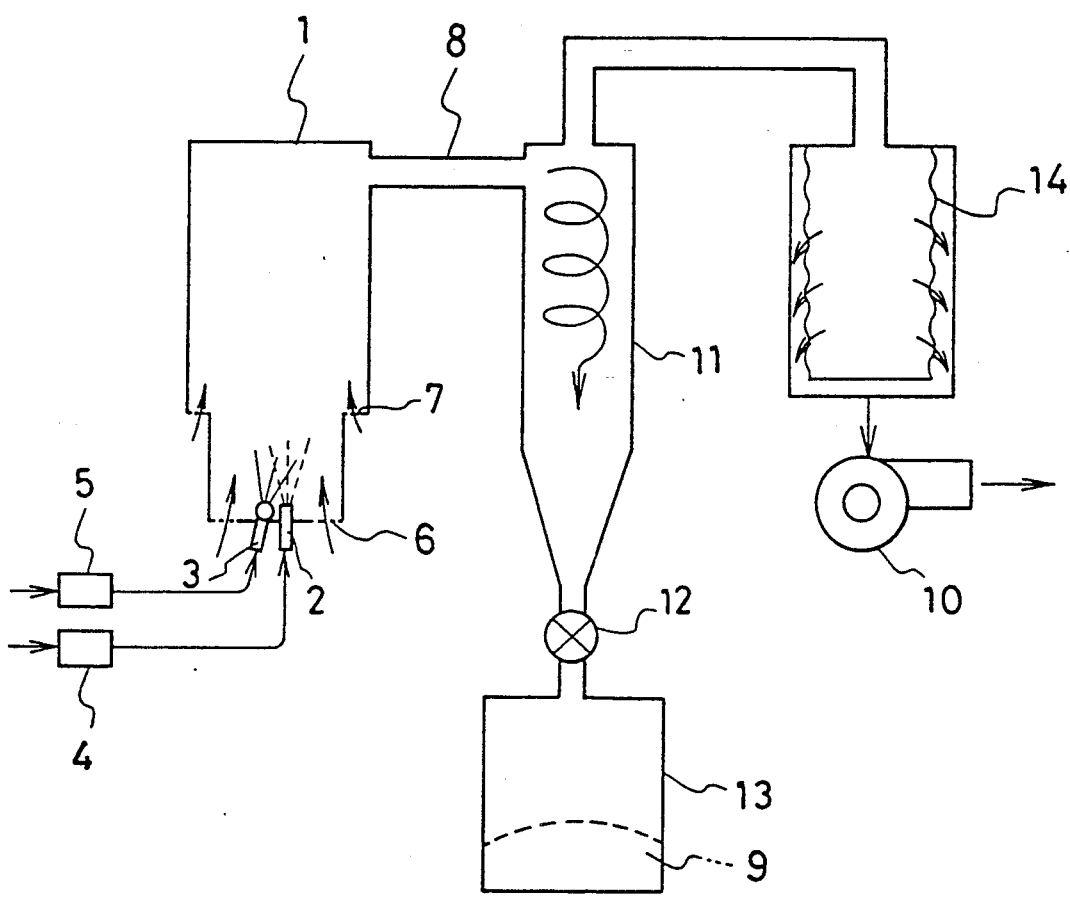
FIG. 1 is a schematic explanatory view showing an embodiment of the granulating and coating apparatus according to the invention.
Figure 2:
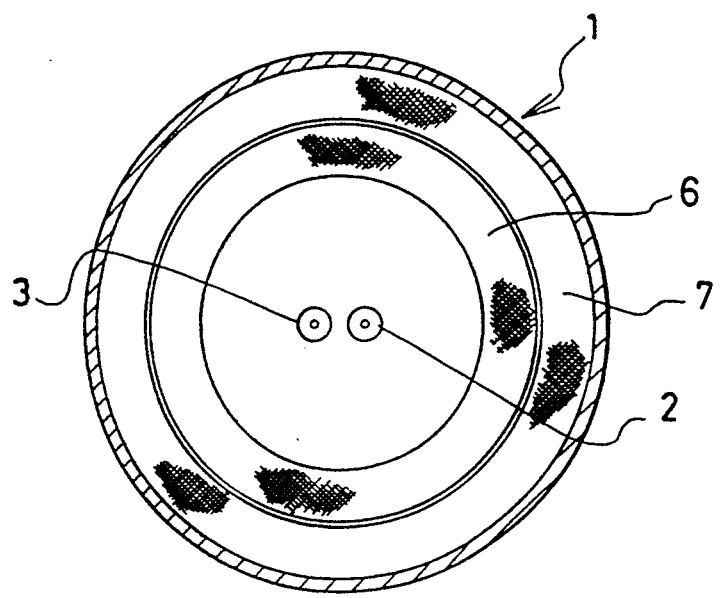
FIG. 2 is a enlarged horizontal sectional view of the processing cylinder 1 of the apparatus in FIG. 1.

FIG. 1 is the schematic explanatory view showing one embodiment of the granulating and coating apparatus according to the present invention, and FIG. 2 is the schematic enlarged horizontal sectional view of a processing cylinder 1.

In the first embodiment, a processing cylinder 1 as being a main body of the apparatus, in which granulating, coating, drying and the like are performed, is of a cylindrical shape, for example with a circular horizontal section having a lower portion of a smaller diameter, and a higher portion of a larger diameter and a stepped portion therebetween as shown in FIGS. 1 and 2.

At the bottom of the processing cylinder 1, there are provided a spray nozzle for supplying a powdery or granular material as being the article to be coated, i.e. a powdery or granular material spray nozzle (means) 2 and another spray nozzle for supplying a coating liquid as being the coating material, i.e. a liquid nozzle (means) 3 in the bottom wall. Both nozzles are directed toward the interior of the processing cylinder 1 and provided in pair at positions adjacent to each other. More specifically, these nozzles 2 and 3 are disposed at positions not being in contact with the air stream dispersed from the adjoining nozzle. In order to supply compressed air to the channels of the nozzles 2 and 3 separately, i.e. independently of each other, respective compressed air sources 4 and 5 are attached to the channels of the nozzles 2 and 3 separately, i.e. independently of each other.

Furthermore, in the bottom wall of the processing cylinder 1, around the nozzles 2 and 3, there is provided an annular cold air supplying opening (cold air supplying means) 6. This cold air supplying opening 6 is formed of a screen or a porous body for example. As the porous body, a metal plate with many pores or a porous sintered plate may be used. The cold air supplied into the processing cylinder 1 from the cold air supplying opening 6 is supplied into a region where the powdery or granular material and the coating liquid from the nozzles 2 and 3 collide with each other.

On the other hand, an annular hot air supplying opening 7 is formed at the stepped portion between the smaller diameter portion and the larger diameter portion of the processing cylinder 1. A diameter of the annulus of the hot air supplying opening 7 is larger than a diameter of the annulus of the cold air supplying opening 6. Furthermore, the hot air supplying opening 7 is provided at a position spaced farther apart in the downstream direction from the nozzles 2 and 3 than the cold air supplying opening 6. Accordingly, the hot air supplied from the hot air supplying opening 7 is supplied to a region spaced in the downstream direction farther apart from the nozzles 2 and 3 than the region where the powdery or granular material and the coating liquid from the nozzles 2 and 3 collide with each other and the cold air is supplied from the cold air supplying opening 6.

Further, at the top portion of the processing cylinder 1, there is provided a catching channel 8 where a product to be coated 9, which has completed the treatments such as the granulating, coating and drying in the processing cylinder 1, is sucked from the interior of the processing cylinder 1 to the outside by a sucking force of a blower 10.

More specifically, the coated product 9, which has been sucked to the outside of the processing cylinder 1 through the catching channel 8, descends in a cyclone 11, passes through a rotary valve 12 and is caught in a recovery container 13. On the other hand, minute particles, dust and the like, which are not usable as the product, do not descend in the cyclone 11, and is caught by a bag filter 14 and removed therefrom.

Action of this first embodiment will hereunder be described.

The raw powdery or granular material as being the article to be coated, which is to be subjected to the granulating and coating treatments, and the coating liquid as being the coating material are blown out into the processing cylinder 1 from the powdery or granular material nozzle 2 and the liquid nozzle 3, respectively. At this time, the blow-out forces from the nozzles 2 and 3 are controlled independently of each other through the adjustment of the air pressures of the respective compressed air sources 4 and 5.

Then the article to be coated and the coating liquid from the respective nozzles 2 and 3 are blown out toward the top wall of the processing cylinder 1 as adjoining slows and collide with each other, whereby the coating liquid uniformly covers the outer peripheries of the article to be coated, so that the granulating and coating can be effected.

In this case, the coating liquid and the article to be coated are not blown out in the directions opposed to each other and toward the inner wall surface of the processing cylinder 1, so that such a disadvantage can be controlled that either one of the blown-out forces becomes excessively larger or smaller than the other, i.e. the coating liquid and the article to be coated adhere to the inner wall surface of the processing cylinder 1 due to the imbalance between the blown-out forces. Furthermore, the so-called "spray dry phenomenon" in which only the coating liquid is accumulated to turn into the particles can be controlled.

Particularly, the cold air from the cold air supplying opening 6 outside the nozzles 2, 3 is supplied to the region where the powdery or granular material and the coating liquid from the nozzles 2 and 3 collide with each other, whereby adhering of the coating liquid and the powdery or granular material to the inner wall surface of the processing cylinder 1 can be prevented, while, since it is the cold air, the "spray dry phenomenon", that the coating liquid is evaporated and solidified into particles before the coating liquid collides with the powdrey or granular material, does not occur, differing from the case in which the hot air is supplied to the region of collision.

On the other hand, the hot air is supplied from the hot air supplying opening 7 to the region above the region of collision and the region to which the cold air is supplied, so that the coating liquid coated on the powdery or granular material can be efficiently dried by this hot air. Furthermore, also by this hot air, the powdery or granular material is prevented from adhering to the inner wall surface of the processing cylinder 1.

The coated article, i.e. the powdery or granular material which has been coated with the coating liquid is dried to a desirable degree by the aforesaid cold air and mainly hot air from the hot air supplying opening 7.

Particularly, in this embodiment, it is possible to effect the efficient and reliable coating with no "spray dry phenomenon" and no adhering to the inner wall surface, by the supply of the cold air to the region of collision and the supply of the hot air to the region upwardly thereof.

As described above, the coated product 9 which has completed the granulating, coating and drying is sucked from the processing cylinder 1, through the catching channel 8 to the cyclone 11 by the sucking force of the blower 10.

In the cyclone 11, the coated product 9 as being a non-defective having a predetermined mass descends through the cyclone 11, passes through the rotary valve 12 and is caught into the recovery container 13.

On the other hand, the minute particles, dust and the like, which have been sucked into the cyclone 11, are sucked toward the bag filter 14 from the top of the cyclone 11 by the sucking force of the blower 10 and caught by the bag filter 14, and thereafter, removed to the outside of the system.

Embodiment 2

Figure 3:
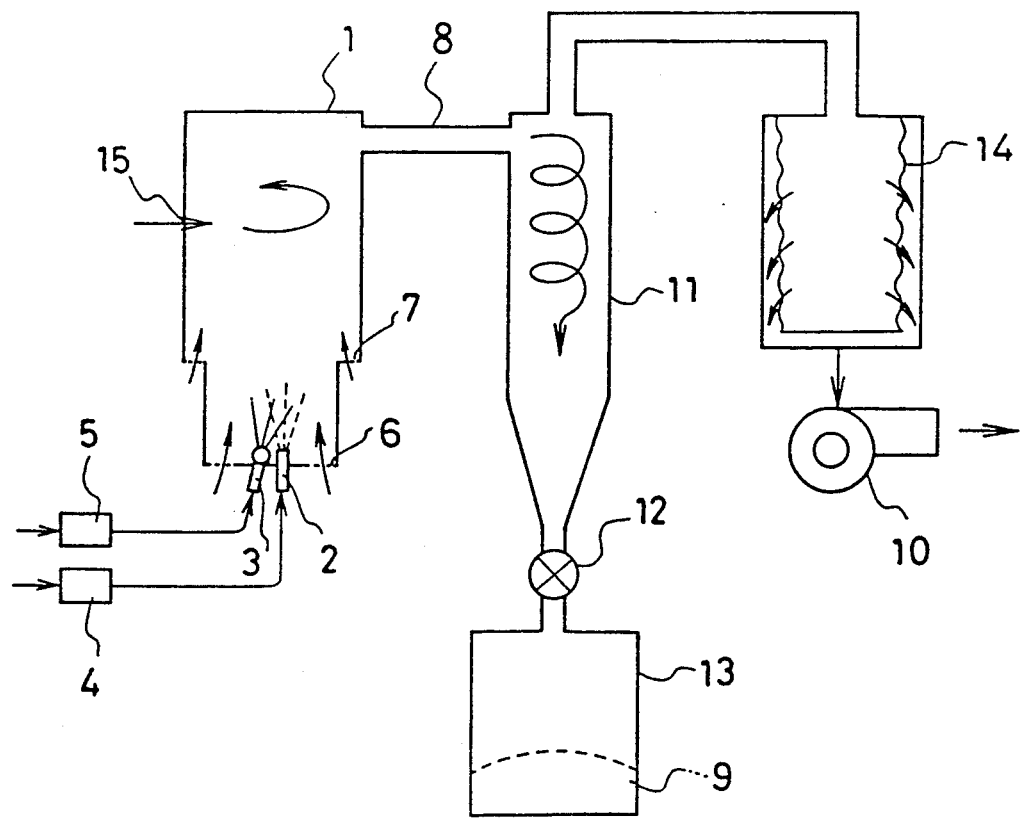
FIG. 3 is a schematic explanatory view showing another embodiment of the granulating and coating apparatus according to the invention.

FIG. 3 is the schematic explanatory view showing another embodiment of the granulating and coating apparatus according to the present invention.

In this second embodiment, a hot air inlet opening 15 as being another hot air supplying means for supplying hot air in a direction tangent to the processing cylinder 1 is provided at the substantially intermediate portion of the larger diameter portion of the processing cylinder 1.

In the case of this second embodiment, the supply of the hot air from the hot air inlet opening 15 is made in the tangential line, therefore the coated product and the hot air are in contact with each other for prolonged time. Further, a substantially volute air stream is formed, so that adhering of the coating liquid and the article to be coated to the inner wall surface of the processing cylinder 1 can be effectively avoided.

EXAMPLE 3

Figure 4:
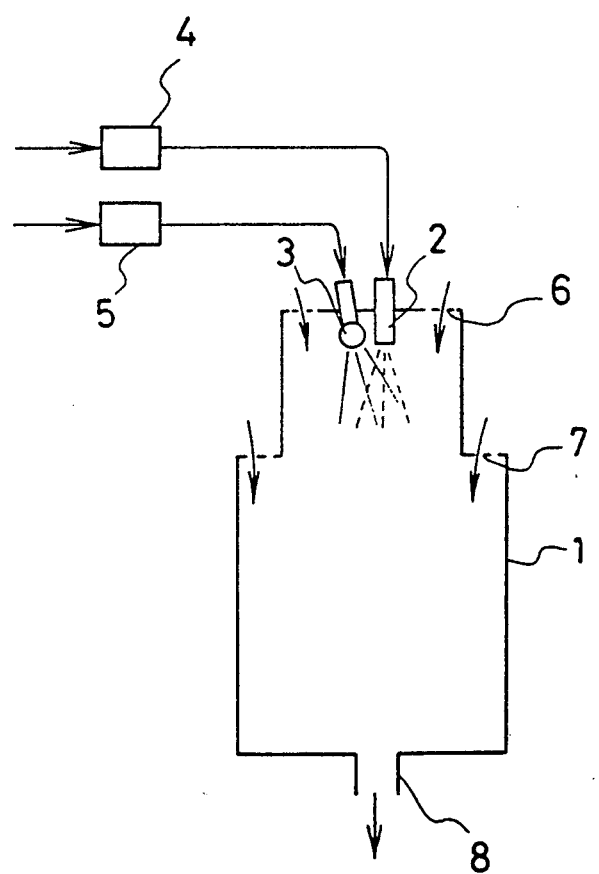
FIG. 4 is a schematic explanatory view showing the essential portions of a further embodiment of the granulating and coating apparatus according to the invention.

FIG. 4 is the schematic explanatory view showing the essential portions of a further embodiment of the granulating and coating apparatus according to the present invention.

In this third embodiment, the powdery or granular material nozzle 2, the liquid nozzle 3 and the cold air supplying opening 6 are provided in the downward direction from the top wall, but not on the bottom wall of the processing cylinder 1, and the hot air supplying opening 7 is positioned downwardly of the cold air supplying opening 6.

Furthermore, in this third embodiment, the nozzles 2 and 3 are directed downwardly, so that the catching channel 8 is provided at the bottom portion of the processing cylinder 1.

In this case, the vertical arrangement of the nozzles 2, 3, the cold air supplying opening 6, the hot air supplying opening 7 and the catching channel 8 is contrary to those shown in the first and second embodiments. However, the order of the coating, drying, catching and the like of the article to be coated and the coating material is the same as those shown in the first and second embodiments. Such functional effects as preventing the coating material from adhering to the inner wall surface of the processing cylinder 1 and also preventing the coating material from being turned into the particles can be obtained similarly to the first and second embodiments.

As has been described hereinabove, the invention achieved by the inventors of the present invention has been described in detail with reference to the embodiments, however, the present invention should not necessarily be limited to the above embodiments, and it is needless to say that the present invention can be variously modified within a scope of the invention.

For example, the positions and the directions of providing the nozzles 2, 3, the cold air supplying opening 6, the hot air supplying opening 7 and the catching channel 8 may be ones other than those in the above embodiments.

The cold air supplying opening 6 and the hot air supplying opening 7 may have constructions other than the annular and porous construction.

Furthermore, the number of the hot air inlet openings 15 may be one or more.

Further, the cross-sectional shape, etc. of the processing cylinder 1 should not necessarily be limited to the above embodiments.

The invention achieved by the inventors can be applied to the granulating, coating and drying of the pharmaceuticals, food products, cosmetics and chemical products. However, this invention can be applied not only to the above materials but also to other materials.

The followings are advantages attained by the typical ones out of the aspects of the invention disclosed in the present application.

(1) The cold air is supplied to the region where the article to be coated and the coating material collide with each other. And the hot air is supplied to the region spaced in the downstream direction farther apart from the both means for supplying the article to be coated and the coating material than this region to which the cold air is supplied. Thereby only the cold air is supplied to the region of collision, and the "spray dry phenomenon" due to the supply of the hot air to the region of collision can be prevented. Further, adhering of the coating material and the article to be coated to the opposed inner wall surface of the processing cylinder and being solidified thereat can be controlled. And moreover, sufficient drying can be achieved and adhering to the inner wall surface can be avoided by the supply of the hot air to the region spaced in the downstream direction apart from the region to which the cold air is supplied.

(2) The section of the route from the collision of the article to be coated with the coating material to the catching thereof is a substantially circular shape, and the inlet direction of the drying air stream is tangent to the section of the circular shape, so that the time, during which the article to be coated and the drying air stream are in contact with each other, can be prolonged, and adhering of the coating material and the like to the inner wall surface can be further effectively controlled by forming the substantially volute air stream.

(3) The means for supplying the article to be coated and the coating material are provided in pair at positions adjacent to each other and not being contact with the air stream dispersed from the adjoining nozzle, so that the adjoining streams are formed in the processing cylinder, and adhering of the coating material and the like to the inner wall surface of the processing cylinder can be controlled.

What is claimed is:

1. A coating method using drying air streams to effectuate coating and drying, comprising the steps of:
   providing a means for supplying a powdery or granular material to be coated and another means for supplying a coating material at such positions that said material to be coated and said coating material collide with each other before said material to be coated and said coating material are dispersed by the drying air streams of cold air and hot air,
   supplying the cold air into a region where said material to be coated and said coating material collide with each other, and
   supplying the hot air to a region spaced in the downstream side farther apart from both means for supplying said material to be coated and said coating material than the region where the cold air is supplied.

2. A coating apparatus using drying air streams to effectuate coating and drying which comprises:
   a processing cylinder,
   a means for supplying a powdery or granular material to be coated and another means for supplying a coating material, both means being provided in the processing cylinder at positions where said material to be coated and said coating material collide with each other before said material to be coated and said coating material are dispersed by the drying air streams of cold air and hot air, cold air supplying means provided outside the both means for supplying said material to be coated and said coating material in the radial direction, and a hot air supplying means provided at a region spaced farther apart from the region of the both means for supplying said material to be coated and said coating material than said cold air supplying means.

3. A coating apparatus as set forth in claim 2, wherein:

said cold air supply means is a porous cold air supplying opening annularly provided around the both means for supplying said material to be coated and said coating material.

4. A coating apparatus as set forth in claim 2, wherein:

said hot air supplying means is a porous hot air supplying opening annularly provided outside said cold air supplying opening in the radial direction.

5. A coating apparatus as set forth in claim 2, wherein:

said both means for supplying the material to be coated and the coating material, said cold air supply means and said hot air supply means are directed upwardly in the processing cylinder to supply the material to be coated, the coating material, the cold air and the hot air, respectively upwardly.

6. A coating apparatus as set forth in claim 2, wherein:

said both means for supplying the material to be coated and the coating material, said cold air supply means and said hot air supply means are directed downwardly in the processing cylinder to supply the material to be coated, the coating material, the cold air and the hot air, respectively downwardly.

7. A coating apparatus as set forth in claim 4, wherein:

said hot air supplying opening is annularly formed in a stepped portion between a smaller-diameter portion and a larger-diameter portion in the processing cylinder.

8. A coating apparatus as set forth in claim 2, wherein:

another hot air supplying means is provided to supply the hot air in a tangent direction to the processing cylinder.

9. A coating apparatus as set forth in claim 2, wherein:

a cyclone is connected through a catching channel to the top of the processing cylinder, and a recovery container is provided under the cyclone.

10. A coating apparatus as set forth in claim 9, wherein:

a bag filter and a means for sucking air within the processing cylinder through said bag filter are connected to the top of the cyclone.

* * * * *